(12) United States Patent
Goto et al.

(10) Patent No.: US 9,501,018 B2
(45) Date of Patent: Nov. 22, 2016

(54) OPTICAL SENSOR, AND DEVICES INCORPORATING THE SAME

(71) Applicants: Kazuma Goto, Miyagi (JP); Fumikazu Hoshi, Miyagi (JP); Yoshihiro Oba, Miyagi (JP)

(72) Inventors: Kazuma Goto, Miyagi (JP); Fumikazu Hoshi, Miyagi (JP); Yoshihiro Oba, Miyagi (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/929,704

(22) Filed: Nov. 2, 2015

(65) Prior Publication Data
US 2016/0154356 A1 Jun. 2, 2016

(30) Foreign Application Priority Data

Nov. 27, 2014 (JP) .................................. 2014-240041
Nov. 28, 2014 (JP) .................................. 2014-241561

(51) Int. Cl.
*G03G 15/00* (2006.01)
*G01N 21/86* (2006.01)
*G01B 11/06* (2006.01)

(52) U.S. Cl.
CPC ....... *G03G 15/5029* (2013.01); *G01B 11/0691* (2013.01); *G01N 21/86* (2013.01); *G01N 2021/8663* (2013.01); *G01N 2201/06113* (2013.01); *G03G 2215/00616* (2013.01); *G03G 2215/00738* (2013.01); *G03G 2215/00751* (2013.01); *G03G 2215/0132* (2013.01)

(58) Field of Classification Search
None
See application file for complete search history.

(56) References Cited

U.S. PATENT DOCUMENTS

| | | | | |
|---|---|---|---|---|
| 5,075,543 A | * | 12/1991 | Courtney | G01V 8/14 250/223 R |
| 5,721,434 A | * | 2/1998 | Siegel | G01N 21/59 250/559.1 |
| 6,215,552 B1 | * | 4/2001 | Acquaviva | G01B 11/0608 356/601 |

(Continued)

FOREIGN PATENT DOCUMENTS

| | | |
|---|---|---|
| JP | 54-080150 | 6/1979 |
| JP | 11-250308 | 9/1999 |

(Continued)

*Primary Examiner* — David Gray
*Assistant Examiner* — Thomas Giampaolo, II
(74) *Attorney, Agent, or Firm* — Oblon, McClelland, Maier & Neustadt, L.L.P.

(57) ABSTRACT

An optical sensor including an abutment part configured to abut one edge of an object to be measured, a wall extending along a side of the object to be measured and having a first opening to pass light emitted to the object to be measured, and a first concave portion formed between the first opening and the abutment part on a side of the wall to position the object to be measured. A paper-type discrimination device including the optical sensor, and a controller configured to discriminate a paper type of the object using the reflection light from the object measured by the optical sensor. An image forming apparatus including the optical sensor or the paper-type discrimination device.

14 Claims, 10 Drawing Sheets

(56) References Cited

U.S. PATENT DOCUMENTS

| | | | |
|---|---|---|---|
| 2003/0235448 A1* | 12/2003 | Nemura | G03G 15/5029 399/389 |
| 2008/0204681 A1* | 8/2008 | Murakami | B41J 11/0035 355/40 |
| 2013/0057868 A1 | 3/2013 | Oba et al. | |
| 2013/0194573 A1 | 8/2013 | Ohba et al. | |
| 2014/0241742 A1 | 8/2014 | Hoshi et al. | |

FOREIGN PATENT DOCUMENTS

| | | |
|---|---|---|
| JP | 2004-179721 | 6/2004 |
| JP | 2006-168858 | 6/2006 |
| JP | 2012-127937 | 7/2012 |
| JP | 2014-163858 | 9/2014 |

* cited by examiner (BRAND-SPECIFIC OUTPUT LEVEL DATA)

| BRAND | S1 | S2 | S3 |
|---|---|---|---|
| A | ... | ... | ... |
| B | ... | ... | ... |
| C | ... | ... | ... |
| D | ... | ... | ... |

OPTICAL SENSOR, AND DEVICES INCORPORATING THE SAME

CROSS-REFERENCE TO RELATED APPLICATIONS

This patent application is based on and claims priority pursuant to 35 U.S.C. §119(a) to Japanese Patent Application Nos. 2014-240041 and 2014-241561, filed on Nov. 27, 2014, and Nov. 28, 2014, respectively, in the Japan Patent Office, the entire disclosure of which is hereby incorporated by reference herein.

BACKGROUND

1. Technical Field

Embodiments of the present invention relate to an optical sensor, a paper-type discrimination device having the optical sensor, and an image forming apparatus having the paper-type discrimination device.

2. Background Art

As an optical sensor that irradiates an object to be measured with light, for example, the technology to discriminate the type of paper by measuring the bumps and dips of the surface of the paper, which is provided for image forming apparatuses such as a copier, facsimile (FAX), and a printer, is known in the art. As such a technology used for paper-type discrimination, optical sensors that irradiate paper with light and use the reflection light from the paper to discriminate the type of the paper are known.

In order to discriminate the types of paper with high accuracy using an optical sensor, it is desired that the irradiating point of light be fixed regardless of the type of the paper. For this reason, a configuration is known in the art in which an opening is formed on a plane having a certain angle with reference to the incidence direction of the light and the light reflected from the portion of the plane exposed by the opening is measured.

SUMMARY

Embodiments of the present invention described herein provide an optical sensor including an abutment part configured to abut one edge of an object to be measured, a wall extending along a side of the object to be measured and having a first opening to pass light emitted to the object to be measured, and a first concave portion formed between the first opening and the abutment part on a side of the wall to position the object to be measured.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

Figure 1:
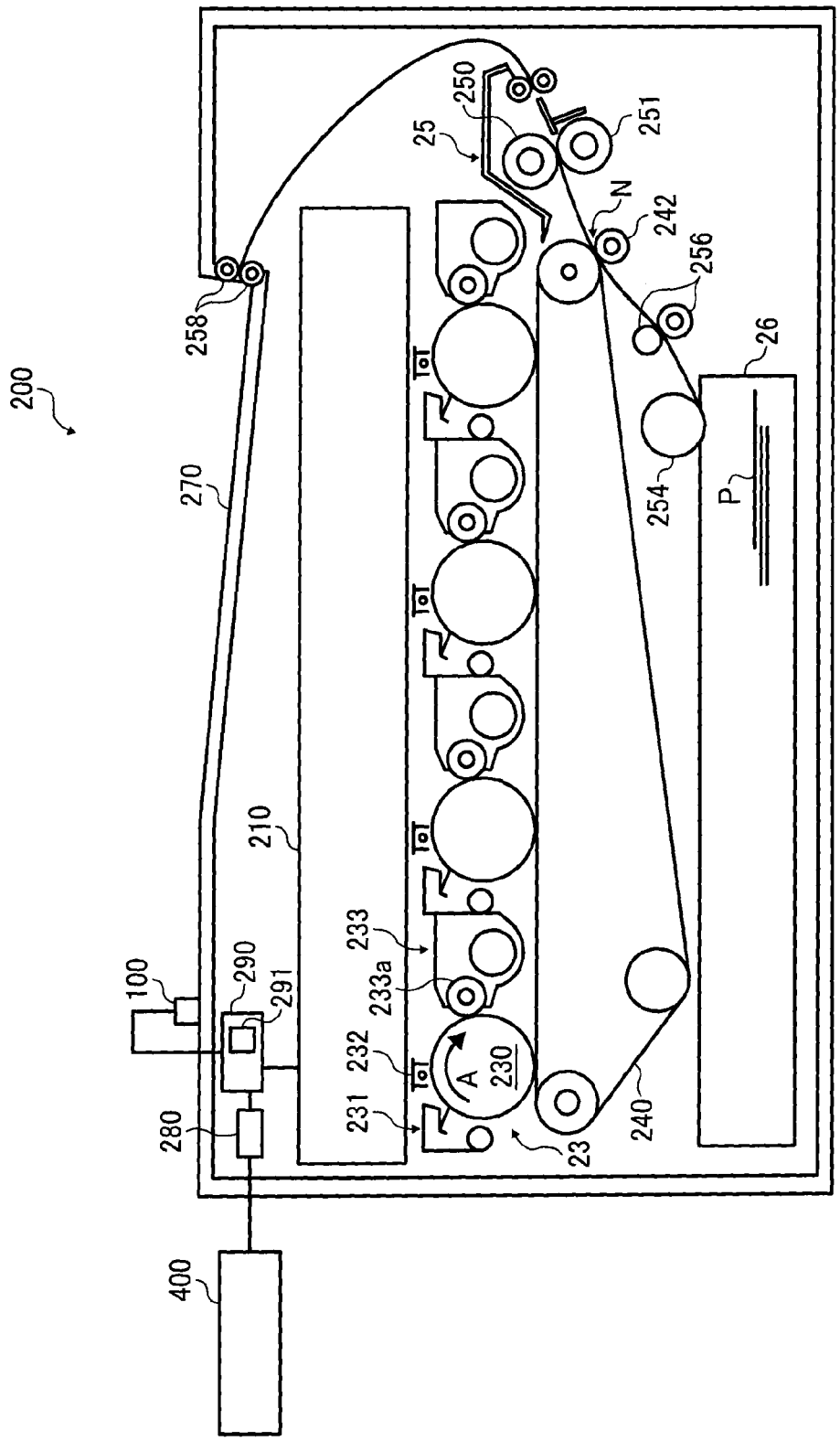
FIG. 1 is a diagram illustrating a schematic configuration of an image forming apparatus according to a first embodiment of the present invention.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, an embodiment of the present invention is described with reference to the drawings. FIG. 1 illustrates an outline of the configuration of an image forming apparatus 200 that serves as an optical sensor according to an embodiment of the present invention.

As illustrated in FIG. 1, the image forming apparatus 200 form an image based on the image data obtained from an externally-provided host device 400, for example, a personal computer (PC). The image forming apparatus 200 includes an image forming unit 23 that forms an image on a transfer belt 240 that serves as an intermediate transferor, and a sheet feeder 26 that feeds paper P to the image forming unit 23.

The image forming apparatus 200 includes a transfer roller 242 that transfers the image formed on the transfer belt 240 to the paper P, i.e., an object to be measured, at a secondary transfer position N, and a fixing device 25 that uses heat and pressure to fix the image transferred at the secondary transfer position N onto the paper P. The image forming apparatus 200 includes a registration roller pair 256 that conveys the paper P fed into the sheet feeder 26 to the secondary transfer position N at a prescribed timing, and an output roller pair 258 that outputs the paper P on which the image has been fixed by the fixing device 25 to a paper output tray 270. The image forming apparatus 200 includes a communication controller 280 that controls bidirectional communication with the host device 400 through the network or the like, and a printer controller 290 that serves as an image-processing controller to control the mechanism related to the image formation performed by the image forming apparatus 200. Further, the image forming apparatus 200 is provided with an optical sensor 100 near the operation panel, in such a manner that an operator can operate the optical sensor 100. The optical sensor 100 irradiates the paper P with light and measures the light reflected from the paper P to discriminate the type of the paper P and obtain paper information Q.

In the present embodiment, cases in which the image forming apparatus 200 is provided with the optical sensor 100 are described. However, the optical sensor 100 may independently be provided. The type of the paper P described herein indicates types including, for example, plain paper, coated paper such as gloss-coated paper, and special paper such as embossed paper. Moreover, the type of the paper P described herein indicates, for example, the quality of paper, the presence of surface treatment such as coating, and the brand of the paper. It is desired that the object to be measured be sheet-shaped or thin-plate-shaped so as to be insertable from a slot 111. Alternatively, the object to be measured may be, for example, a cloth, cutting sheet, or a substrate, other than the paper P that serves as a recording medium. In such cases, the type of the object to be measured includes, for example, a material such as vinyl, cloth, and plastic, presence of surface treatment, the brand, and the surface condition.

The image forming unit 23 is accommodated in the image forming apparatus 200 to serve as a unit of four image forming stations that correspond to the basic colors of cyan, magenta, yellow, and black, respectively. For the purpose of simplification, only one of the four image forming stations of the image forming unit 23 is described, and the description of the other similarly-configured three image forming stations is omitted. The image forming unit 23 includes a drum-shaped photoconductor 230 that serves as a latent-image bearer, an optical scanner 210 that serves as an exposure device and optically-writing unit to form a latent image on the photoconductor 230, and a developing device 233 that forms a toner image on the photoconductor 230 on which the latent image has been formed. The image forming unit 23 includes a cleaning device 231 that removes the toner from the photoconductor 230 after the toner image formed on the photoconductor 230 has been transferred to the transfer belt 240, and a charging device 232 that electrically charges the photoconductor 230 from which the toner has been removed. The photoconductor 230, the charging device 232, the cleaning device 231, and the developing device 233 are used as a unit and together configure an image forming station.

The photoconductor 230 is a drum-shaped rotor on which a photosensitive layer is formed, and the photosensitive layer is a surface to be scanned by the scanning light of the optical scanner 210. The photoconductor 230 is driven by a driver in A-direction as illustrated in FIG. 1.

The charging device 232 is a charger disposed on a downstream side of the cleaning device 231, on an upstream side of the optical scanner 210 in the A-direction. The charging device 232 evenly charges the surface of the photoconductor 230. The charging device 232 may perform charging by corona discharge, or may use a charging brush or a charging roller to perform charging.

The optical scanner 210 scans each of the surfaces of the electrically-charged photoconductor 230, with the scanning light that is modulated for each color based on the multicolor image data received from the printer controller 290. By so doing, an electrostatic latent image that is drawn by electrical potential is formed on the surface of the photoconductor 230.

The developing device 233 thinly and evenly applies the toner of the corresponding color onto the surface of a development roller 233a by rotating the development roller 233a. When the toner that has been applied to the surface of the development roller 233a is brought into contact with the surface of the photoconductor 230 of the corresponding color, the toner moves and adheres only to the portions of the surface of the photoconductor 230 that are irradiated with the scanning light, i.e., the portions exposed by the scanning light. In other words, the developing device 233 renders the latent image manifest by making the toner adhere to the latent image formed on the photoconductor 230, to form a toner image on the photoconductor 230.

The toner images that are formed on the photoconductors 230 are sequentially transferred to the transfer belt 240 at specified timing according to transfer bias. Then, the transferred toner images of the four basic colors are superimposed on top of one another to form a multicolor image.

A sheet feeder 26 includes a sheet tray that accommodates the paper P, and a plurality of feeding rollers 254 that convey the paper P accommodated in the sheet tray towards the registration roller pair 256.

The fixing device 25 includes a heating roller 251 having a heat source inside, and a pressure roller 250 that forms a fixing nip together with the heating roller 251. The paper P bearing a toner image runs through the fixing nip of the fixing device 25, and the toner image is fixed by heat and pressure on the surface of the paper T. The heating roller 251 includes a cylinder roller made of aluminum, a silicone rubber layer formed around the peripheral surface of the cylinder, and a halogen heater disposed inside the cylinder.

The printer controller 290 includes, for example, a central processing unit (CPU), a read-only memory (ROM) in which a program described by CPU-readable codes and various kinds of data used for executing the program are stored, and a random access memory (RAM) that serves as a working memory. In the printer controller 290, a plurality of types of the paper P that can be used for the image forming apparatus 200 are stored. Moreover, in the printer controller 290, the image-forming conditions that are optimal for each of the types of the paper P, i.e., image-processing conditions such as development conditions, exposure conditions, and transfer conditions, are stored as a development and transfer table 291 (see FIG. 7).

Note that the development conditions include, for example, the toner concentration at the developing device 233, and developing bias. The exposure conditions include, for example, the intensity of the laser beam emitted from the optical scanner 210 to the photoconductor 230, i.e., the latent-image writing intensity. The latent-image writing intensity is equivalent to the scanning light intensity. The transfer conditions include, for example, a primary transfer bias, i.e., the potential difference with which the toner image is transferred from the photoconductor 230 to the transfer belt 240, or a primary transfer current value, i.e., the current value with which the toner image is transferred from the photoconductor 230 to the transfer belt 240. Moreover, the transfer conditions include, for example, a secondary transfer bias, i.e., the potential difference with which the image is transferred from the transfer belt 240 to the paper P, or a secondary transfer current value, i.e., the current value with which the image is transferred from the transfer belt 240 to the paper P.

Figure 2:
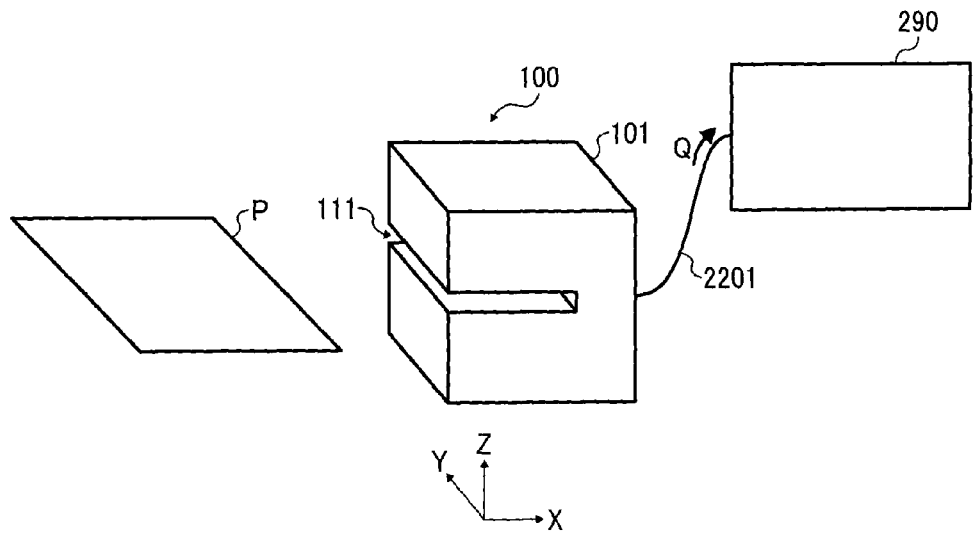
FIG. 2 is a diagram illustrating a schematic configuration of a paper-type discrimination device according to the first embodiment of the present invention.

FIG. 2 is a diagram illustrating an example of a schematic configuration of a paper-type discrimination device according to the present embodiment. As illustrated in FIG. 2, the optical sensor 100 is connected to the printer controller 290 through a cable 2201, and the optical sensor 100 sends the paper information Q to the printer controller 290 through the cable 2201. Moreover, the optical sensor 100 includes a housing 101, and a slot 111 into which the paper P is inserted in the X direction. The X direction may be referred to as an insertion direction.

Figure 3:
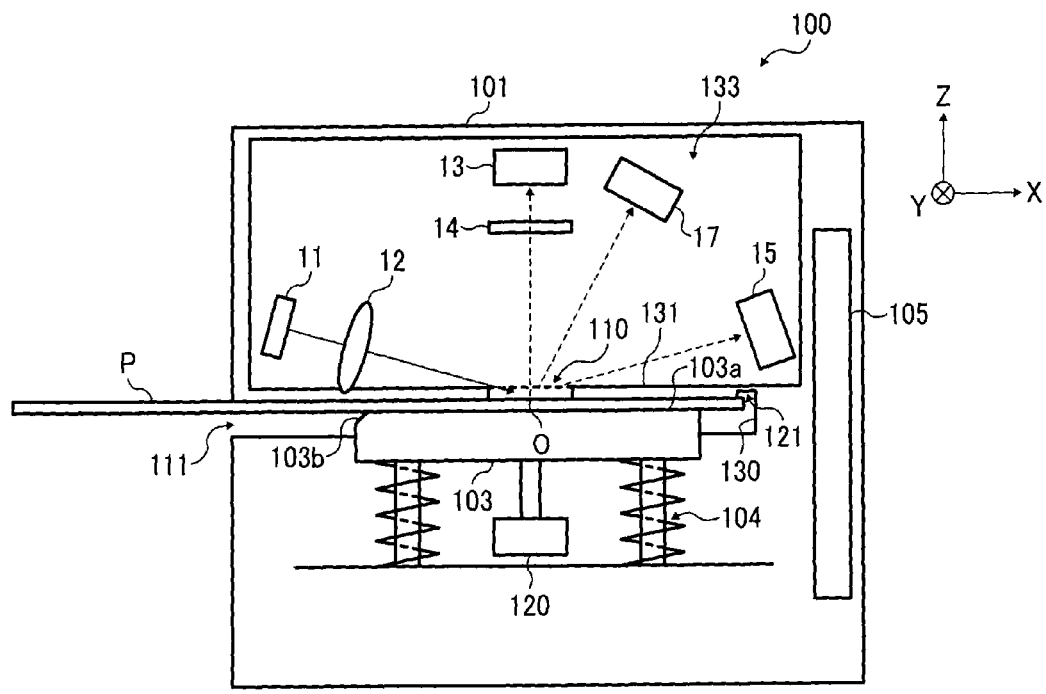
FIG. 3 is a diagram illustrating a schematic configuration of an optical sensor according to the first embodiment of the present invention.

FIG. 3 is a diagram illustrating an example configuration of the optical sensor 100 according to the present embodiment. As illustrated in FIG. 3, the optical sensor 100 is arranged on the other side of the slot 111. In other words, the optical sensor 100 is arranged at an end in the X direction. Moreover, the optical sensor 100 includes an abutment part 130 that contacts one edge of the paper P to perform positioning for the paper P, and a wall 131 that abuts one of the surfaces of the paper P. Moreover, the optical sensor 100 includes a first aperture 110 that is formed on the wall 131 to irradiate an irradiation center O, which is any desired part on the paper P, with light, and a first concave portion 121 that has a concave shape in the normal direction of the Z-axis and is formed between the first aperture 110 and the abutment part 130 on the wall 131 side.

Moreover, the optical sensor 100 includes a light source 11 that is disposed in the normal direction of the Z-axis with reference to the wall 131 inside the housing 101, and a collimator lens 12 that collimates the light emitted from the light source 11. Moreover, the optical sensor 100 includes a detector 133 having three photodetectors that measure the reflection light from the paper P. Moreover, the optical sensor 100 includes a supporting member 103 that presses the paper P against the wall 131 or the periphery of the first aperture 110 from the other side of the wall 131. Note that the supporting member 103 serves as a pressurizer in the present embodiment. Further, the optical sensor 100 includes a controller 105 that controls the signals of the elements of the optical sensor 100.

The housing 101 is a box made of aluminum, and the surface of the housing 101 is anodized in black in order to reduce the influence of disturbance light and stray light. The slot 111 is formed to have a continuous opening to three planes including the front plane of the optical sensor 100 in the reverse direction of the X-axis of the housing 101, the side planes orthogonal to the Y-axis.

The cable 2201 is a route of power supply that connects the printer controller 290 to the optical sensor 100. The cable 2201 may be, for example, a universal serial bus (USB) cable or an RS-232C. Moreover, the cable 2201 is a transmission route through which the paper information Q such as the reflectance measured by the optical sensor 100 is transmitted to the printer controller 290.

The abutment part 130 is a part of the housing 101 that is a plane orthogonal to the X-axis, and is arranged at the end of the slot 111 in the X direction. The wall 131 abuts the surface of the paper P in a state where one edge of the paper P in the normal direction of the X-axis contacts the abutment part 130, and supports the paper P with supporting member 103 parallel to the XY plane. Moreover, the wall 131 has the first aperture 110 that is circularly formed around the point of the irradiation center O at which the light emitted from the light source 11 is emitted. It is desired that the first aperture 110 be disposed near the center of the paper P that is in a state of contact.

Figure 4A:
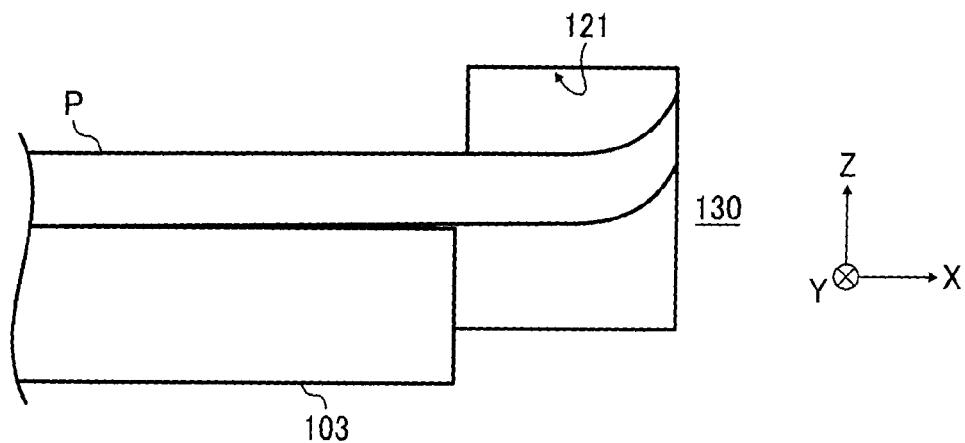
FIG. 4A and FIG. 4B are schematic diagrams illustrating a feature of the first embodiment of the present invention.
Figure 4B:
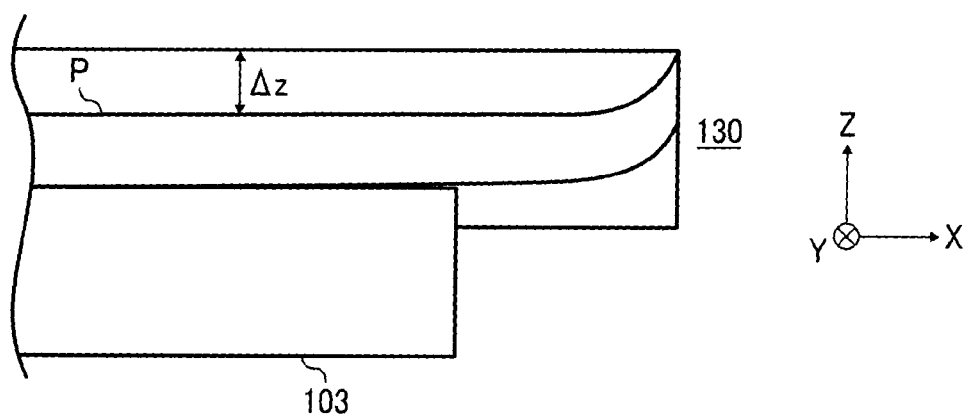

FIG. 4A and FIG. 4B are schematic diagrams illustrating a feature of the first embodiment of the present invention. The first concave portion 121 is a recess formed at a portion between the first aperture 110 and the abutment part 130, and may be a notch or hole, or a trench. As illustrated in FIG. 4A and FIG. 4B, the first concave portion 121 is arranged such that the edge of the paper P in the normal direction of the X-axis, in a state of contact, can enter the inside of the first concave portion 121.

The supporting member 103 includes a pressing plane 103a that is arranged opposed to the wall 131 to press the paper P against the wall 131, a leg part that supports the pressing plane 103a, and a spring 104 that is provided for the leg part to serve as a pressing member. Moreover, the supporting member 103 includes a paper-thickness sensor 120 that measures the displacement caused on the pressing plane 103a in the Z-axis direction. At the edge of the supporting member 103 on the upstream side of the insertion direction (i.e., at the edge of the supporting member 103 in the reverse direction of the X-axis), an inclined portion 103b that is inclined with reference to the pressing plane 103a is formed to make the insertion of the paper P easier. In an initial state where the paper P has not yet been inserted, the supporting member 103 is pressed against the wall 131 in the normal direction of the Z axis due to the force exerted by spring 104. In other words, the supporting member 103 is maintained in a state where the pressing plane 103a contacts the wall 131.

The paper-thickness sensor 120 is a displacement converter in a cantilevered state, and is attached to the supporting member 103. The paper-thickness sensor 120 measures the displacement of the supporting member 103 when the supporting member 103 moves down due to the insertion of the paper P. In other words, the paper-thickness sensor 120 measures the displacement caused on the pressing plane 103a in the Z-axis direction, with reference to the position of the pressing plane 103a that abuts the wall 131 in the initial state. More specifically, the paper-thickness sensor 120 outputs to the controller 105 pulse signals whose number of the signals is proportional to the amount of displacement of the cantilever, and the controller 105 counts the number of the pulse signals. Accordingly, the amount of the displacement of the cantilever is calculated. In the present embodiment, the paper-thickness sensor 120 is a displacement converter in a cantilevered state. However, the paper-thickness sensor 120 may be a noncontact displacement gage using laser, or a differential-transformer displacement gage.

The light source 11 is a semiconductor laser beam source having a vertical-cavity surface-emitting laser (VCSEL) array where a plurality of VCSEL elements are two-dimensionally arranged. The light emitted from the light source 11 is collimated by the collimator lens 12, and the collimated laser-beam bundle is emitted to the irradiation center O. As described above, the first aperture 110 is arranged around the irradiation center O formed on the wall 131. Accordingly, when the paper P is in a state of contact, the light passes through the first aperture 110 and is emitted to the paper P.

Assuming that the light is incident on the boundary surface of a medium, i.e., the boundary surface between the paper P and the air in the present embodiment, the plane that includes the incident light beam and the normal line drawn from the point of incidence of the boundary surface is referred to as an incidence plane. As the light source 11 includes a plurality of two-dimensionally arranged laser-light emitting elements, there are a plurality of incidence planes whose number is equal to the number of the laser-light emitting elements. However, for the sake of explanatory convenience, the incidence plane of the light that enters the irradiation center O is referred to as the incidence plane of light source 11 on the paper P. In other words, the plane that includes the irradiation center O and is parallel with the XZ-plane is the incidence plane in the present embodiment.

The light that is polarized in the direction perpendicular to the incidence plane is referred to as an S-polarized light, and the light that is polarized in the direction perpendicular to the S-polarized light is referred to as a P-polarized light. In other words, the light where the oscillating direction is perpendicular to the XZ plane is the S-polarized light, and the light where the oscillating direction is parallel to the XZ plane is the P-polarized light. In the following description, for the purpose of simplification, the terms "S-polarized light" and "P-polarized light" are also used for the reflection light as long as the polarization direction of the reflection light is equivalent to the polarization direction of the light that enters the paper P.

Figure 5:
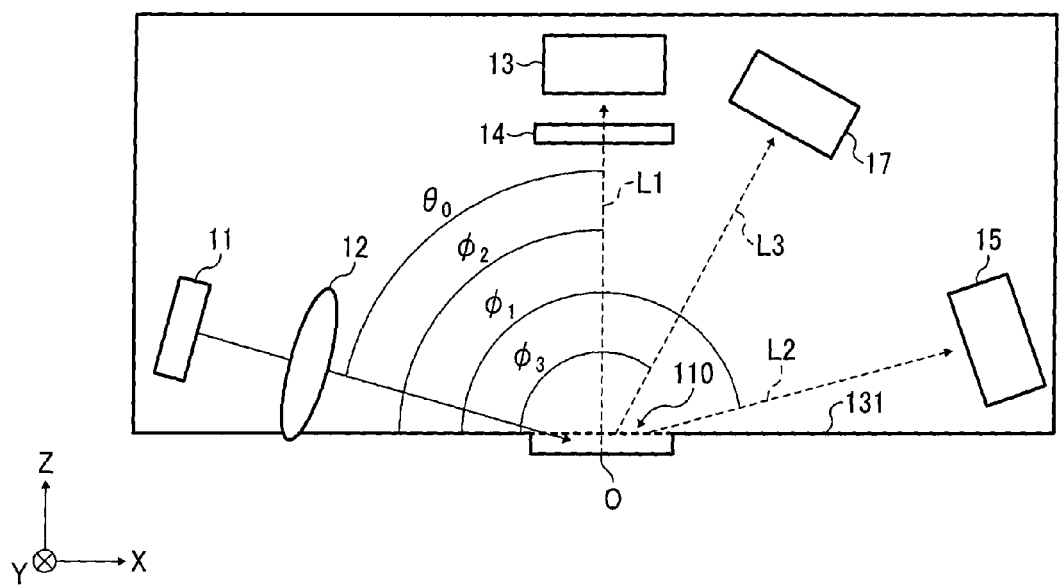
FIG. 5 is a schematic diagram of an example of the reflection light measurement of the optical sensor illustrated in FIG. 3.

FIG. 5 is a schematic diagram of an example of a reflection light measurement of the optical sensor 100 illustrated in FIG. 3, according to the present embodiment. The light emitted from the light source 11 is a linearly polarized light, and irradiates the surface of the paper P with the S-polarized light having the first polarization direction. Note that the angle which the straight line connecting between the light source 11 and the irradiation center O forms with the Z-axis in FIG. 5, i.e., the incidence angle $\theta_0$ from the light source 11 is 80 degree.

The detector 133 includes a first photodetector 15 arranged on an optical path of the light that is emitted from the light source 11 and then is reflected at the irradiation center O by specular reflection, a polarizing filter 14 that is arranged above the irradiation center O in the Z-axis direction, and a second photodetector 13 that is arranged above the polarizing filter 14 along the extension drawn from the irradiation center O to the polarizing filter 14. Moreover, the detector 133 includes a third photodetector 17 that is arranged at a position different from that of the first photodetector 15 in the normal direction of the X-axis with reference to the irradiation center O. Each of the first photodetector 15, the second photodetector 13, and the third photodetector 17 may be, for example, a photodiode.

The controller 105 includes, for example, an analog-to-digital (A/D) converter that A/D converts the output from the first photodetector 15, the second photodetector 13, and the third photodetector 17, a microcontroller that controls the operation of the sensor system, a memory, and a logical circuit.

As illustrated in FIG. 5, the first photodetector 15 is arranged such that the angle $\phi_1$ which the surface of the paper P forms with a line L2 connecting the irradiation center O to the first photodetector 15 is 170 degrees.

The polarizing filter 14 is a deflector that transmits the P-polarized light and blocks the S-polarized light. Alternatively, the polarizing filter 14 may be a polarization beam splitter that selectively transmits the P-polarized light and the S-polarized light in a similar manner to a deflector. The second photodetector 13 is arranged along the extension drawn from the irradiation center O to center of the polarizing filter 14, in the normal direction of the Z axis. As illustrated in FIG. 5, the angle $\phi_2$ which the surface of the paper P forms with the line L2 connecting through the irradiation center O, the polarizing filter 14, and the center of the second photodetector 13, is 90 degrees.

The third photodetector 17 is arranged such that the angle $\phi_3$ which the surface of the paper P forms with a line L3 connecting the irradiation center O to the center of the third photodetector 17 is 120 degrees.

It is desired that the irradiation center, the center of the light source 11, the center of the first photodetector 15, the center of the second photodetector 13, and the center of the third photodetector 17 be disposed on substantially the same XZ plane, and approximately be disposed on the incidence plane.

The light that is emitted from the light source 11 and enters the paper P may be classified into two kinds of reflected light, consisting of the light reflected at the surface of the paper P, and the light that enters the inside of the paper P and then is reflected inside the paper P. Further, the light reflected at the surface of the recording paper may be classified into two kinds of reflected light, consisting of the light of regular reflection and the light of diffuse reflection. Regarding the light that is reflected inside the paper P, multiple scattering occurs in the fibers inside the paper P. Accordingly, it is considered that only the diffuse-reflected light is detectable.

Figure 6A:
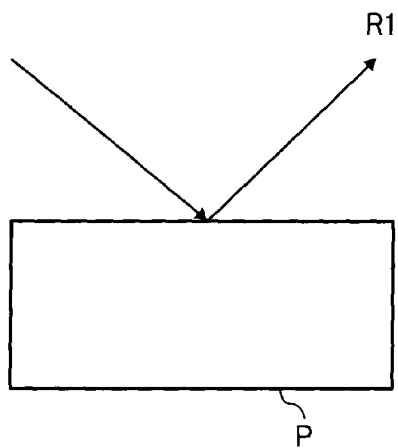
FIG. 6A, FIG. 6B, and FIG. 6C are diagrams illustrating examples of the reflection light that is measured by the reflection light measurement illustrated in FIG. 5.
Figure 6B:
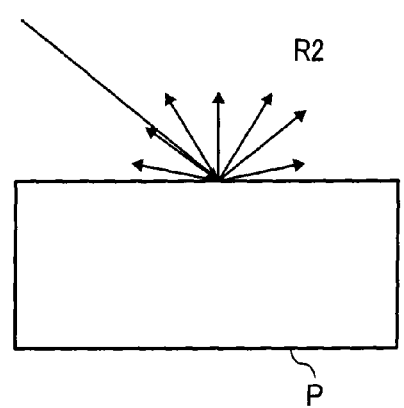
Figure 6C:
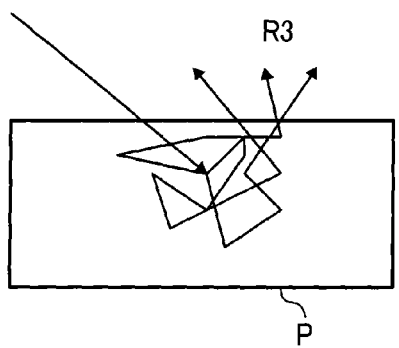

FIG. 6A, FIG. 6B, and FIG. 6C are diagrams illustrating examples of the reflection light that is measured by the reflection light measurement illustrated in FIG. 5, according to the present embodiment. The reflection light of the light that is emitted from the light source 11 and then enters the paper P is schematically classified into three kinds of reflection light, as illustrated in FIG. 6A, FIG. 6B, and FIG. 6C. FIG. 6A illustrates a surface specular reflection light R1 that is reflected by specular reflection on the surface of the paper P. FIG. 6B illustrates a surface diffuse reflection light R2 that is reflected by diffuse reflection on the surface of the paper P. FIG. 6C illustrates an internal diffusion reflection light R3 that is reflected by diffuse reflection inside the paper P.

Here, relation between types of the paper P and the above-described reflection lights are described. Firstly, when the paper P has smooth paper quality on its surface and almost no penetration into the paper P occurs, it is assumed that almost all the incident light is reflected on the surface by specular reflection and almost all the reflection light is detected as the surface specular reflection light R1.

Secondly, when the surface of the paper P has some bumps and dips, it is schematically considered that planar portions and uneven portions are distributed over the surface of the paper P at a constant rate according to the type of the paper P. In such cases, the light reflected at the planar portions are detected as the surface specular reflection light R1, and the light reflected at the uneven portions are detected as the surface diffuse reflection light R2. Assuming that the planar portions and the uneven portions appear at random, the surface diffuse reflection light R2 is theoretically isotropic on the XZ plane.

The internal diffusion reflection light R3 is a light that enters the inside of the paper P and then returns to the incidence plane as reflected. Accordingly, it is considered that the intensity of the internal diffusion reflection light R3 varies according to the density or thickness of the paper P.

Moreover, it is considered that the internal diffusion reflection light R3 is isotropic because the internal diffusion reflection light R3 can be reflected in any direction in the XYZ space.

Note that in order for the light reflected at the surface of the paper P to have components other than the S-polarized light, i.e., in order for the polarization direction to rotate on the surface of the paper P, the incident light needs to be reflected at a portion of the surface that is inclined in the direction perpendicular to the incidence plane. However, the irradiation center, the center of the light source 11, the center of the first photodetector 15, the center of the second photodetector 13, and the center of the third photodetector 17 are disposed on substantially the same XZ plane. Accordingly, the light that is reflected at a portion of the surface that is inclined in the direction perpendicular to the incidence plane is not detected by the detector 133. Accordingly, both the surface specular reflection light R1 and the surface diffuse reflection light R2 are on the incidence plane. For this reason, it is considered that the polarization direction of the surface specular reflection light R1 and the surface diffuse reflection light R2 are substantially the same as that of the incident light and the S-polarized light.

On the other hand, the polarization direction of the internal diffusion reflection light R3 rotates while passing through fibers and going through multiplex polarization. The internal diffusion reflection light R3 may include the P-polarized components. In other words, only the internal diffusion reflection light R3 includes the P-polarized light on the XZ plane when it is assumed that the light source 11 only emits the S-polarized linear light. For this reason, the polarizing filter 14 is arranged between the second photodetector 13 and the irradiation center O to block the S-polarized light and transmit only the P-polarized light. In other words, the polarization direction of the light emitted from the light source 11 is offset from the light transmitted by the polarizing filter 14 by 90 degrees. Accordingly, the second photodetector 13 detects only the P-polarized components included in the internal diffusion reflection light R3. According to the experiments run by the inventor and his associates, it is known that the amount of the P-polarized components included in the internal diffusion reflection light R3 is dependent on the length of the path in the fibers of the paper P through which the light passes and thus correlates with the thickness or density of the paper P.

As the incidence angle $\theta_0$ has 80 degrees, the reflection angle $\theta_{R1}$ of the surface specular reflection light R1 also has 80 degrees. Accordingly, almost all the surface specular reflection light R1, and some of the surface diffuse reflection light R2 and the internal diffusion reflection light R3 enter the first photodetector 15. In other words, the first photodetector 15 mainly receives the surface specular reflection light R1. Note that the surface diffuse reflection light R2 isotropically disperses on the XZ plane. Accordingly, it is considered that the amount of the surface diffuse reflection light R2 received by the first photodetector 15 is approximately equal to the amount of the surface diffuse reflection light R2 received by the third photodetector 17. On the other hand, the third photodetector 17 barely receives the surface specular reflection light R1. For this reason, the surface specular reflection light R1 and the surface diffuse reflection light R2 can separately be measured by calculating the difference between the output signal level of the first photodetector 15 and the output signal level of the third photodetector 17.

As described above, the optical sensor 100 according to the present embodiment includes the detector 133 that uses the first photodetector 15, the second photodetector 13, and the third photodetector 17 to measure the reflection light from the paper P.

Figures 7, 8:
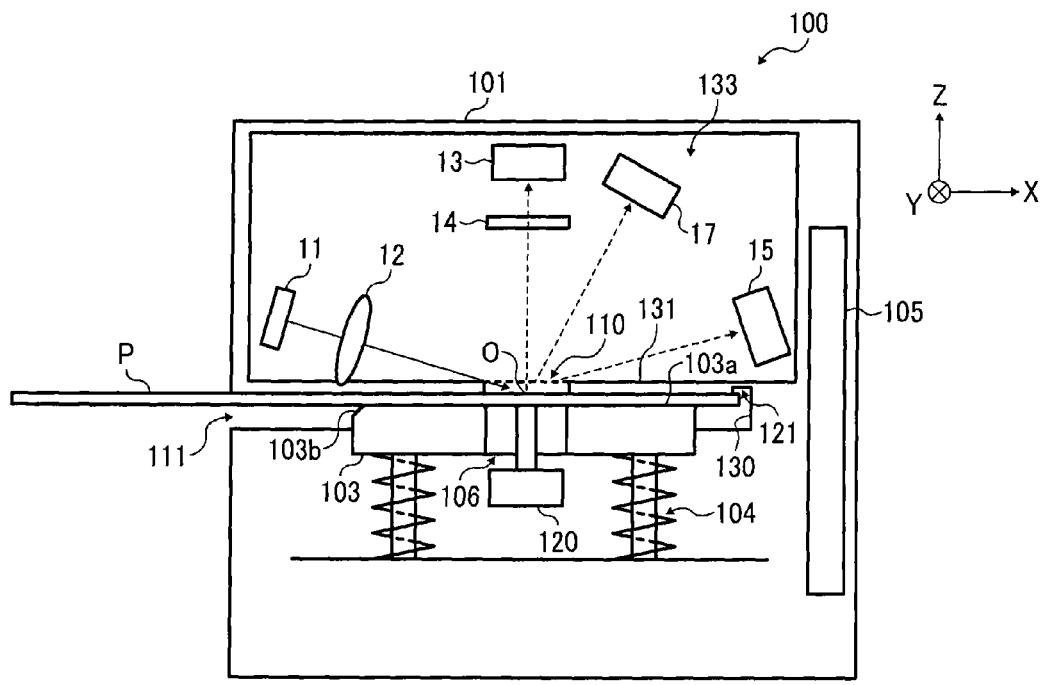
FIG. 7 is a diagram illustrating an example of paper information according to the first embodiment of the present invention.
FIG. 8 is a diagram illustrating an example configuration of an optical sensor according to a second embodiment of the present invention.

The optical sensor 100 controls the switching on and off of the light source 11 to irradiate the paper P with light according to the instruction given from the printer controller 290 through the cable 2201 or the instruction given from the host device 400, and measures the output of each of the photodetectors of the detector 133. Moreover, the optical sensor 100 sends the measured signal values S'$_1$, S'$_2$, and S'$_3$, which are the results of the measurement performed by each of the photodetectors, to the printer controller 290. FIG. 7 is a diagram illustrating an example of paper information according to the present embodiment. As illustrated in FIG. 7, the printer controller 290 can discriminate the paper information Q of the paper P by checking the measured signal values S1', S'2, and S'3 against the database that is input in advance. As described above, the optical sensor 100 and the printer controller 290 together serve as a paper-type discrimination device that discriminates the paper information Q using the reflection light of the paper P measured by the optical sensor 100.

The image forming operation that is performed by the image forming apparatus 200 according to the present embodiment is described. Firstly, the image data that is input from the host device 400 is transmitted by the communication controller 280 to the printer controller 290 through the network or the like, and is stored in the ROM provided inside the printer controller 290 as image data. The paper P is set to the optical sensor 100 to determine the type of the paper P. Then, the paper P is set to the sheet tray of the sheet feeder 26. In so doing, the paper information Q indicating the type of the paper P is stored in the printer controller 290. The paper information Q is checked against the development and transfer table 291 stored in the printer controller 290, and the optimal image-processing conditions that are in conformity with the characteristics of the paper information Q are selected from the development and transfer table 291.

The sheet feeder 26 conveys the paper P set to the sheet tray to the registration roller pair 256 using the feeding roller 254. When the sheet feeder 26 starts the sheet feeding operation as above, the image forming unit 23 performs the latent-image writing operation, the development of a toner image, and the primary transfer from the photoconductor 230 to the transfer belt 240 as described above, based on the image-processing conditions and the image data stored in the printer controller 290. After the primary transfer of the image onto the transfer belt 240 is performed and the color toner image is developed, the registration roller pair 256 conveys the paper P at a prescribed timing such that at the secondary transfer position N, the position of the toner image on the transfer belt 240 matches the position of the paper P on which the image is to be formed. At the secondary transfer position N, the paper P is sandwiched between the transfer roller 242 and the transfer belt 240 and the secondary transfer bias is applied thereto. Accordingly, the secondary transfer of the toner image is completed. After the paper P passes through the fixing nip of the fixing device 25 and the toner image formed on the surface of the paper P is fixed by the application of heat and pressure, the paper P is ejected by the output roller pair 258 to the paper output tray 270.

Next, a method of discriminating the paper-type information Q of the paper P with the use of the optical sensor 100 according to the present example embodiment is described in detail.

In the initial state of the optical sensor 100, the pressing plane 103a and the wall 131 are maintained in a state of contact. When the paper P is inserted into the slot 111, the paper P is inserted between the pressing plane 103a and the wall 131 along the inclined portion 103b. When the paper P is inserted, the front side of the paper P abuts the wall 131, and the back side of the paper P abuts the pressing plane 103a, while the paper P pressing down the supporting member 103. Then, an edge of the paper P on the downstream side of the insertion direction abuts the abutment part 130.

In that state of abutment, cases in which a burr is formed on the edge of the paper P that abuts the abutment part 130, as illustrated in FIG. 4A and FIG. 4B, are described. When such a burr is present, as illustrated in FIG. 4B, a gap Δz may appear between the first aperture 110 and the paper P when the paper P is simply abutted against the wall 131 as in the related art. Note that the gap Δz is the misalignment between the first aperture 110 and the paper P. It is considered that when such a gap Δz appears, the position of the irradiation center O varies according to, for example, the degree of the burr, the difference in the paper quality of the paper P, and the degree of the resilience of the paper P. When the position of the irradiation center O varies, it is considered that the incidence angle varies and the intensity of each of the surface specular reflection light R1, the surface diffuse reflection light R2, and the internal diffusion reflection light R3 also varies. Moreover, it is considered that stray light entering through the gap Δz also has an adverse effect on the measurement precision.

In order to avoid such situation, as described above, the optical sensor 100 according to the present embodiment includes the first concave portion 121 that is formed between the first aperture 110 and the abutment part 130 on the wall 131 side. Due to the provision of the first concave portion 121, as described above with reference to FIG. 4A, the burr of the edge of the paper P is accommodated in the first concave portion 121. Accordingly, the gap Δz due to the burr of the edge of the paper P is reduced or prevented, and the reflection light can precisely be measured. In other words, the first concave portion 121 can prevent the object to be measured from being misaligned from the first aperture 110.

The intensity of the output signals measured by the first photodetector 15, and the second photodetector 13, and the third photodetector 17 when the paper P is in a state of abutment and irradiated with the light emitted from the light source 11 are referred to as the measured signal values $S'_1$, $S'_2$, and $S'_3$, respectively. In the development and transfer table 291 stored in the printer controller 290, as illustrated in FIG. 7, the intensities of the output signals that are measured in advance are stored as reference signal values $S_1$, $S_2$, and $S_3$ together with the paper-type information Q. More specifically, the reference signal values $S_1$, $S_2$, and $S_3$ and the paper-type information Q are stored as a database in association with the image-processing conditions. The combinations of the reference signal values $S_1$, $S_2$, and $S_3$ may be stored as a paper discrimination database, which is independent of the development and transfer table 291. Alternatively, the data may be stored in an external device other than the printer controller 290, for example, in the host device 400, and the data may be exchanged through the communication enabled, for example, by the Internet.

The printer controller 290 compares the measured signal values $S'_1$, $S'_2$, and $S'_3$ with the reference signal values $S_1$, $S_2$, and $S_3$, respectively, to calculate a relevance ratio R as depicted in Formula 1 below.

$$R = \left(1 - \left|\frac{S_1 - S'_1}{S_1 + S'_1}\right|\right) \times \left(1 - \left|\frac{S_2 - S'_2}{S_2 + S'_2}\right|\right) \times \left(1 - \left|\frac{S_3 - S'_3}{S_3 + S'_3}\right|\right) \quad \text{[Formula 1]}$$

The printer controller 290 specifies the type of paper with the highest relevance ratio R from the types of paper associated with the reference signal values $S_1$, $S_2$, and $S_3$, and displays the specified type of paper as a result of paper discrimination. The printer controller 290 obtains optimal image-processing conditions for the result of paper discrimination from the development and transfer table 291, and controls the elements of the image forming apparatus 200 based on the obtained optimal image-processing conditions. Due to the configuration described above, the printer controller 290 serves as an adjuster that adjusts the image-processing conditions of the image forming apparatus 200 according to the type of the paper P.

The optical sensor 100 includes the detector 133 that measures the light reflected from the paper P, and the light source 11 that emits the light. Note that the light is the S-polarized linear light. The detector 133 includes the first photodetector 15 arranged on an optical path of the surface specular reflection light R1, and the second photodetector 13 that is arranged in the optical path of the internal diffusion reflection light R3 on the XZ plane and detects the bundle of the P-polarized light that is orthogonal to the S-polarized light. Due to this configuration described above, not only the surface specular reflection light R1 and the surface diffuse reflection light R2 but also the internal diffusion reflection light R3 including the density information of the inside of the paper P or the like are measured. Accordingly, the types of the paper P including the surface condition and the brand of the paper P can precisely be discriminated. Moreover, the detector 133 includes the third photodetector 17 that is arranged in the optical path of the surface diffuse reflection light R2 outside the optical path of the surface specular reflection light R1. Due to the configuration described above, the surface specular reflection light R1 and the surface diffuse reflection light R2 can separately be measured by calculating the difference between the output signal level of the first photodetector 15 and the output signal level of the third photodetector 17. Accordingly, the reflection light can more precisely be measured.

The optical sensor 100 includes supporting member 103 that applies pressure so as to press the paper P against the wall 131 when the paper P is in a state of abutment. Due to the configuration described above, the gap Δz between the first aperture 110 and the paper P can further be reduced, and the reflection light can precisely be measured.

The paper-thickness sensor 120 measures the displacement caused on the supporting member 103 in the Z-axis direction to measure the thickness of the paper P. The type of the object to be measured is discriminated based on the reflection light and the thickness measured by the paper-thickness sensor 120. Due to the configuration described above, not only the light reflected from the paper P but also the thickness of the paper P are measured. Accordingly, the types of the paper P can further precisely be discriminated.

The optical sensor 100 includes the slot 111 into which the paper P is inserted in the X direction, i.e., the insertion direction, along the wall 131. Due to the configuration described above, the edge of the paper P in the X direction abuts the abutment part 130, and thus the reflection light can easily be measured when the paper P is in a state of abutment.

In the optical sensor 100 according to the present embodiment, the light emitting elements provided for the light source 11 are vertical-cavity surface-emitting laser (VCSEL) elements, and the light source 11 has a VCSEL array where a plurality of VCSEL elements are two-dimensionally arranged. Due to the configuration described above, the laser beams can be integrated with high density, and thus the light quantity increases and the signal-to-noise ratio (S/N) can be improved. Accordingly, the precision of the discrimination can be improved. Moreover, as the contrast ratio of the speckle pattern of reflection light decreases by switching on all the light-emitting points at the same time, the precision of the discrimination can further be improved. As the laser beams are integrated with high density, the laser beams concentrate around the optical axis of the collimator lens 12. Accordingly, the laser beams can easily be collimated without depending on the quality of the collimator lens 12, and the incidence angle on the paper P can be made uniform. Accordingly, the precision of the discrimination can be improved.

Next, a second embodiment of the present invention is described. In the following embodiments, only the features unique to each embodiment will be described, and the description of the features in common with the first embodiment is omitted.

FIG. 8 is a diagram illustrating an example configuration of the optical sensor 100 according to a second embodiment of the present invention. In second embodiment of the present invention, as illustrated in FIG. 8, the supporting member 103 of the optical sensor 100 includes a second aperture 106.

The paper-thickness sensor 120 according to the second embodiment is arranged such that the cantilevered portion of the paper-thickness sensor 120, which is the measuring part of the paper-thickness sensor 120, penetrates the second aperture 106 and abuts the paper P. In other words, the paper-thickness sensor 120 abuts the portion of the paper P exposed at the second aperture 106. Due to the configuration described above, the paper P can directly be measured without depending on the irregularities in the thickness of the components of the supporting member 103. Accordingly, the thickness of the paper P can more precisely be measured.

Figure 9:
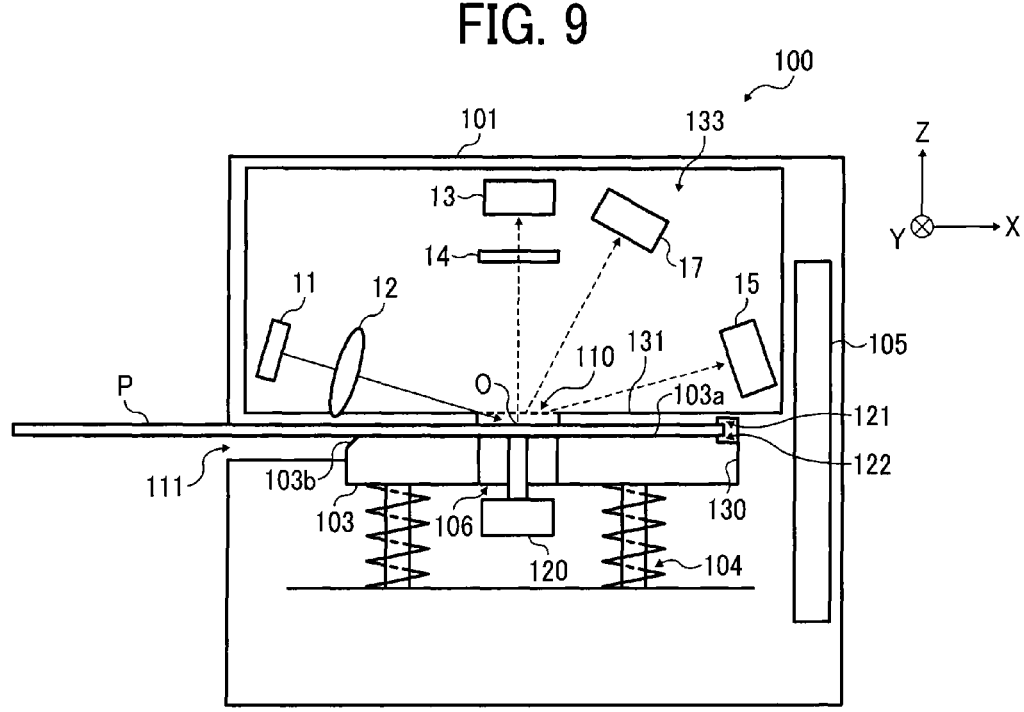
FIG. 9 is a diagram illustrating an example configuration of an optical sensor according to a third embodiment of the present invention.

Next, a third embodiment of the present invention is described. FIG. 9 is a diagram illustrating an example configuration of the optical sensor 100 according to the third embodiment of the present invention. In third embodiment of the present invention, as illustrated in FIG. 9, the supporting member 103 of the optical sensor 100 includes a second concave portion 122, in addition to the configuration of the second embodiment described above. The second concave portion 122 may be referred to as a second notch. In other words, the optical sensor 100 has the second concave portion 122 that is formed so as to be opposed to the first concave portion 121, on the other side of the paper P. Due to the configuration described above, when a burr of the edge of the paper P remains in any of the upper and lower side of the Z direction, the edge of the paper P can be accommodated in one of the first concave portion 121 and the second concave portion 122. Accordingly, the gap Δz is reduced, and the light reflected from the paper P can precisely be measured. Note that the second concave portion 122 may be a trench or a hole.

Figure 10:
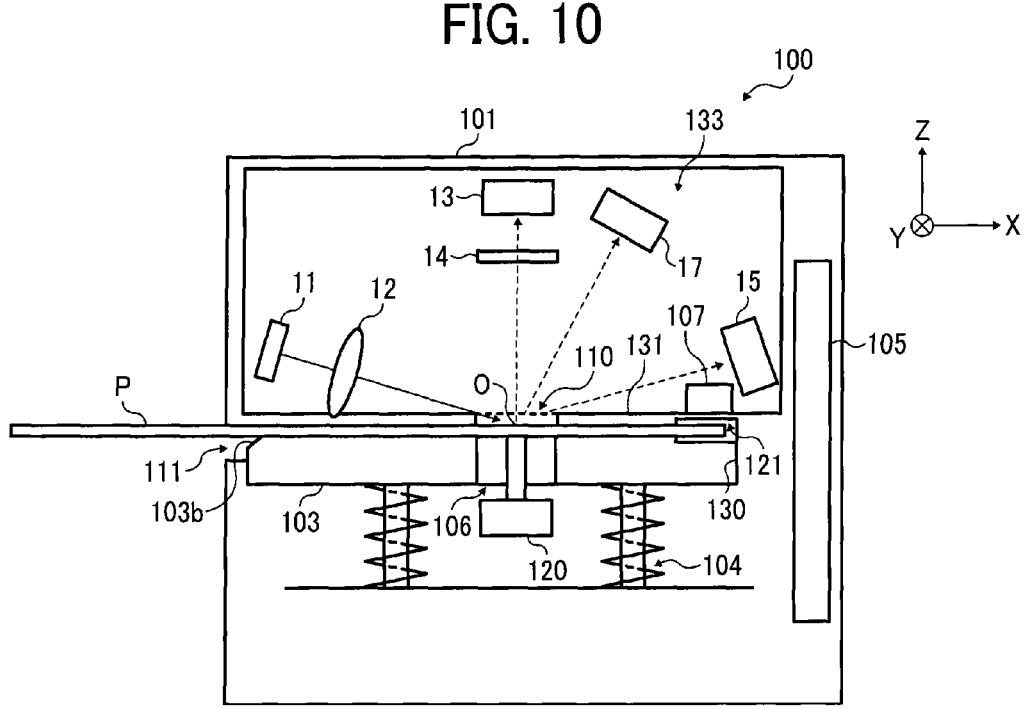
FIG. 10 is a diagram illustrating an example configuration of an optical sensor according to a fourth embodiment of the present invention.

Next, a fourth embodiment of the present invention is described. FIG. 10 is a diagram illustrating an example configuration of the optical sensor 100 according to the fourth embodiment of the present invention. In the fourth embodiment, as illustrated in FIG. 10, the optical sensor 100 includes an edge sensor 107 that is provided at an end portion of the slot 111 to detect that an edge of the paper P has passed while moving in the X direction. The edge sensor 107 is provided on a downstream side of the first aperture 110 in the X direction, near the first concave portion 121 in the X direction. The edge sensor 107 is, for example, a reflective photointerrupter including a pair of light emitting elements and light receiving elements, and detects whether or not the paper P has passed under the edge sensor 107.

Figure 11:
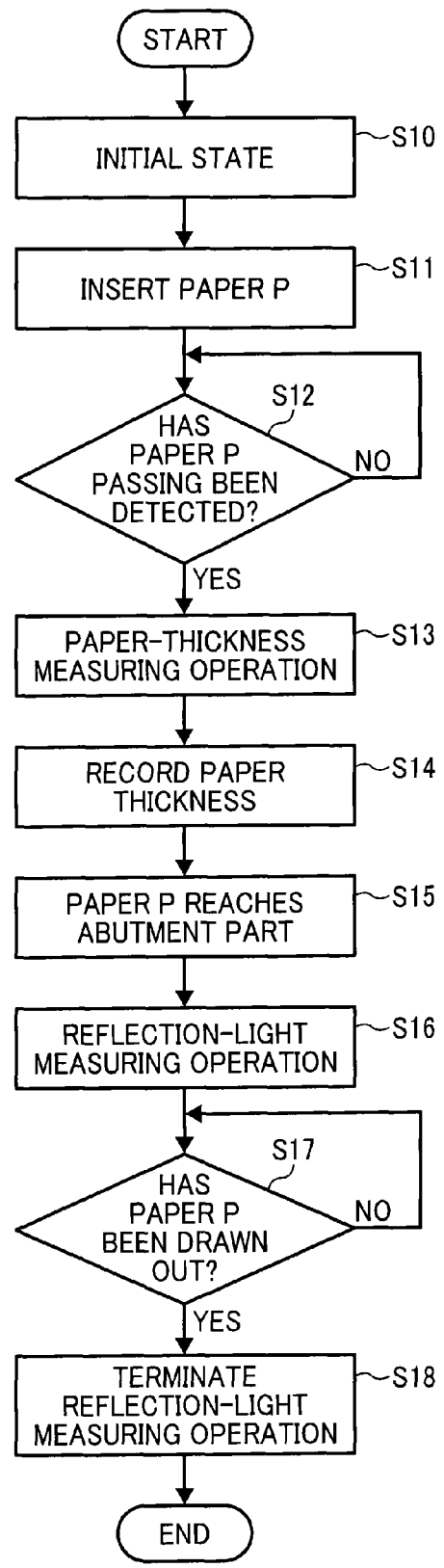
FIG. 11 is a block diagram depicting example processes performed by the optical sensor illustrated in FIG. 10.

FIG. 11 is a block diagram depicting example processes performed by the optical sensor 100 illustrated in FIG. 10. The measuring operation of the optical sensor 100 according to the fourth embodiment is described with reference to FIG. 11. In the initial state of the optical sensor 100, in a similar manner to the first embodiment described above, the pressing plane 103a and the wall 131 are maintained in a state of contact (S10). When the paper P is inserted through the slot 111, the paper P moves forward in the X direction while pressing down the supporting member 103 (S11).

When an edge of the paper P passes under the edge sensor 107, the light emitted from the light emitting elements of the edge sensor 107 is reflected by the paper P and enters the light receiving elements of the edge sensor 107. Accordingly, the edge sensor 107 detects the paper P passing underneath (S12). The controller 105 uses the paper-thickness sensor 120 to measure the thickness of the paper P when the edge sensor 107 has detected the paper P passing underneath (S13). This measuring operation is referred to as a paper-thickness measuring operation. Then, the controller 105 records the smallest value while the paper P is passing as the thickness of the paper P (S14). After an edge of the paper P reaches the abutment part 130 (S15), the paper P is pulled out in the −X direction. It is to be noted that the edge sensor 107 keeps detecting the paper P passing underneath until the edge of the paper P has been pulled out and passed under the edge sensor 107.

When the edge sensor 107 has detected the paper P passing underneath and the edge of the paper P has been moved to a downstream side in the X direction of the edge sensor 107, the controller 105 controls the light source 11 to irradiate the paper P with light, and controls the detector 133 to measure the light reflected from the paper P (S16). This measuring operation is referred to as a reflection-light measuring operation.

In the optical sensor 100, the paper P is securely inserted between the first aperture 110 and the supporting member 103 as described above, and the thickness of the paper P can be measured in a condition that an edge of the paper P is accommodated in the first concave portion 121. Accordingly, the thickness of the paper P can precisely be measured. Moreover, as the reflection-light measuring operation is performed while the paper P is inserted and pulled out as described above, the reflection light can be measured at a plurality of positions on the paper P. In such cases, it is desired that the averages of the respective measured signal values $S'_1$, $S'_2$, and $S'_3$ be used for the paper discrimination. When the averages of the measured signal values $S'_1$, $S'_2$, and $S'_3$ are used as described above, the distribution of the surface condition or fiber density inside the paper P is balanced, and the effect of variation can be reduced. Accordingly, the precision of the paper-type discrimination improves.

When the edge of the paper P further moves towards the −X direction, the edge sensor 107 detects that the paper P has been drawn out (S17). When it is detected that the paper P has been drawn out, the controller 105 controls the light source 11 to cease irradiation, and terminates measuring the reflected light (S18). Due to the configuration described above, the reflection light and the thickness of the paper P are measured only when the paper P is placed between the first aperture 110 and the supporting member 103 with reliability. Accordingly, the power consumption can be reduced while the paper P is not inserted.

Note that the edge sensor 107 may be provided on an upstream side of the first concave portion 121, while the edge sensor 107 is on a downstream side of the first aperture 110 in the X direction. In such cases, the detector 133 starts measuring the reflection light after the edge sensor 107 has detected the paper P passing and a prescribed length of time according to the insertion speed of the paper P has passed. Moreover, the edge sensor 107 may be a contact-type sensor, and may detect the paper P passing when an edge of the paper P touches the edge sensor 107.

Figure 12:
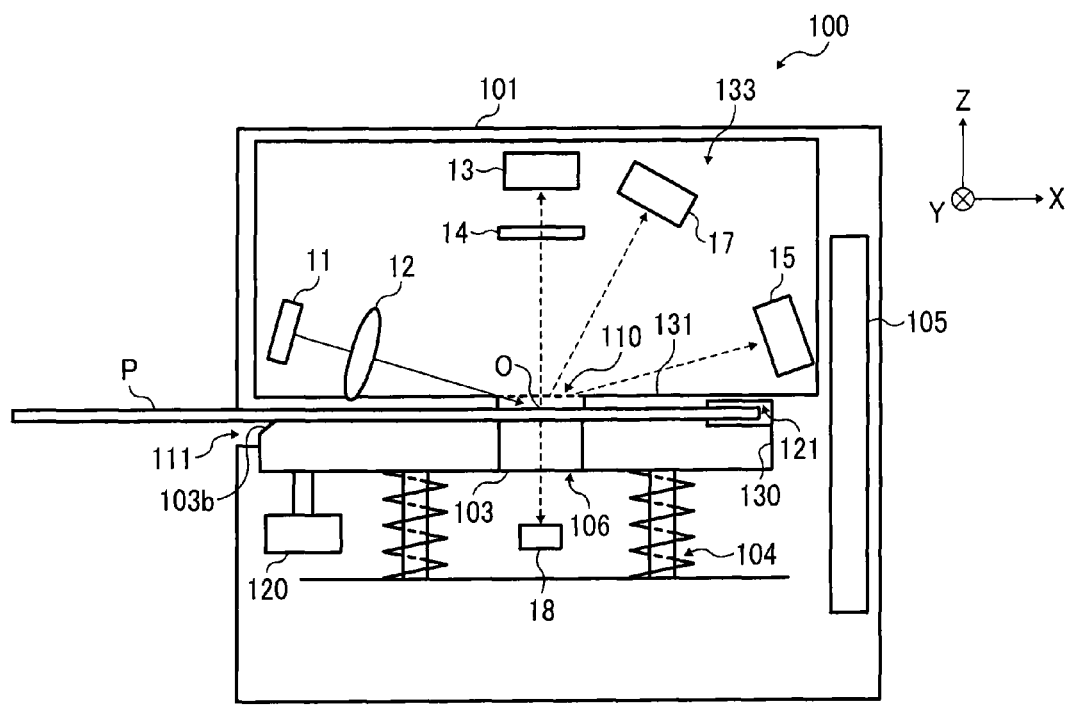
FIG. 12 is a diagram illustrating an example configuration of an optical sensor according to a fifth embodiment of the present invention.

In the following description, a fifth embodiment of the present invention is described with reference to FIG. 12. FIG. 12 is a diagram illustrating an example configuration of the optical sensor 100 according to the fifth embodiment of the present invention. In the fifth embodiment, a third aperture 106 that serves as a light transmitting part is formed at a position opposed to the first aperture 110 having the paper P therebetween, such that the center of the third aperture 106 is on a straight line drawn from the irradiation center O parallel to the Z-axis. Moreover, a transmission-light detector 18 that detects the light quantity of the light that has passed through the third aperture 106 is disposed below the center of the third aperture in the Z-axis direction. The transmission-light detector 18 detects the internal diffusion reflection light R3 that dispersed inside the paper P. Due to the configuration described above, the transmission-light detector 18 measures a measured signal value $S'_4$ that indicates the characteristics of the paper P such as the thickness or fiber density of the paper P. The precision of the discrimination improves by using the measured signal value $S'_4$ described above together with the measured signal values $S'_1$, $S'_2$, and $S'_3$ for the paper-type discrimination of the paper P.

Figure 13:
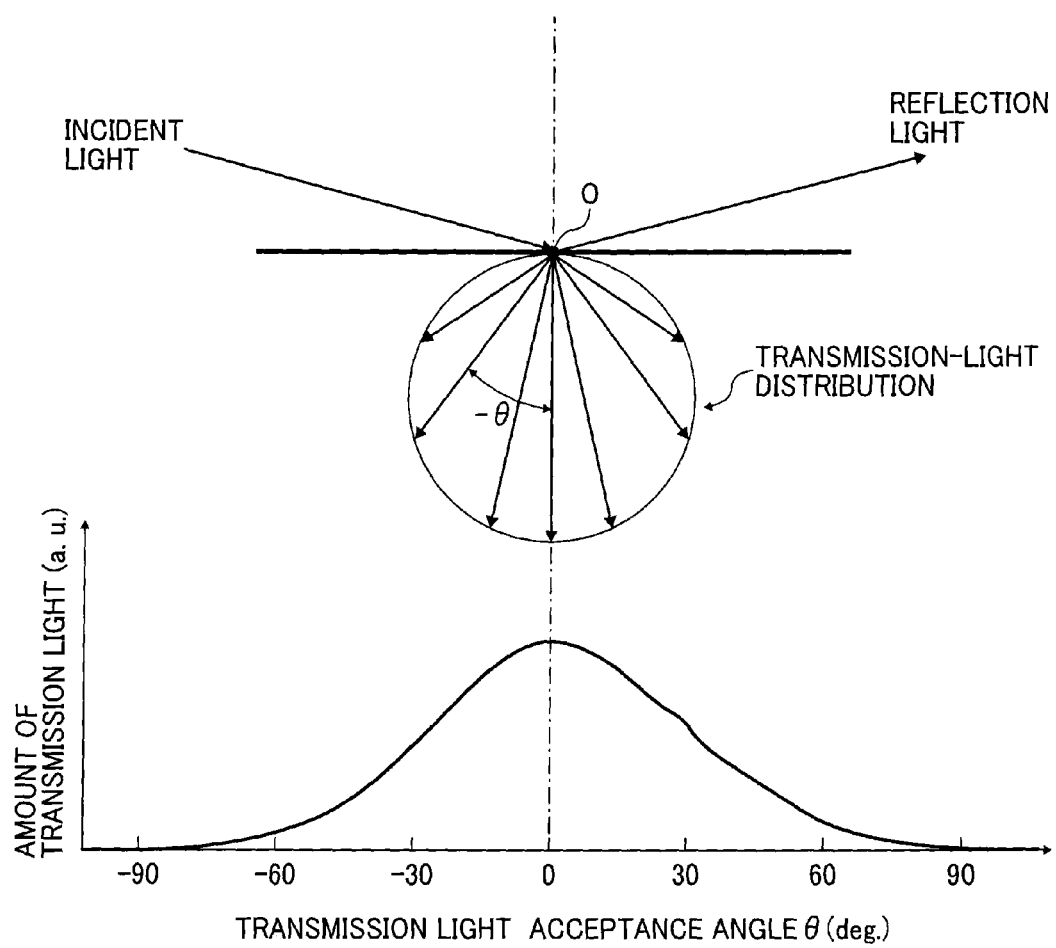
FIG. 13 is a diagram illustrating an example of the intensity distribution of the transmission light measured by the transmission-light detector illustrated in FIG. 12.

FIG. 13 is a diagram illustrating an example of the intensity distribution of the transmission light measured by the transmission-light detector 18 illustrated in FIG. 12. As illustrated in FIG. 13, it is known by experiment that the intensity distribution of the light that passes through the paper P has a peak in the reverse direction of the Z-axis under the irradiation center O. For this reason, in order to obtain a high signal-to-noise ratio (S/N), it is desired that the transmission-light detector 18 be disposed in the reverse direction of the Z-axis under the irradiation center O.

The present invention is not limited to the details of the example embodiments described above, and various modifications and improvements are possible.

For example, the image forming apparatus 200 in the embodiments described above may be an optical plotter or a digital photocopier. In the above embodiments, cases in which the image forming apparatus 200 is provided with four photoconductors were described. However, the image forming apparatus 200 may be a monochrome image forming apparatus or an inkjet image forming apparatus. Although it is desired that the detector 133 have a plurality of photodetectors, the detector 133 may be provided with only one photodetector.

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

What is claimed is:

1. An optical sensor comprising:
    an abutment part configured to abut one edge of an object to be measured;
    a wall extending along a side of the object to be measured and having a first opening to pass light emitted to the object to be measured;
    a first concave portion formed between the first opening and the abutment part to position the object to be measured; and
    a pressurizer configured to press the object against the wall.

2. The optical sensor according to claim 1, further comprising: a second concave portion formed between the first opening and the abutment part so as to face the first concave portion via the object to be measured.

3. The optical sensor according to claim 1, further comprising:
    a light transmitting part formed on an opposite side of the first opening with reference to the object, the light transmitting part covering apart of the first opening or an entirety of the first opening; and
    a transmission-light detector configured to detect an amount of the light that has passed through the light transmitting part.

4. The optical sensor according to claim 1, further comprising:
    a light source configured to emit the light, the light being linearly polarized light having a first polarization direction; and
    a detector configured to measure a reflection light of the light emitted to the object, the detector including:
    a first photodetector disposed on an optical path of the light reflected from the object, and
    a second photodetector disposed on an optical path of bundle of lights reflected by diffuse reflection from an incidence plane of the object and configured to detect the bundle of lights of a second polarization direction orthogonal to the first polarization direction.

5. The optical sensor according to claim 4, wherein
    the light source includes a light emitting element, and
    the light emitting element is a vertical-cavity surface-emitting laser elements.

6. The optical sensor according to claim 1, wherein the object is inserted into a slit that extends along the wall in an insertion direction parallel to the wall.

7. The optical sensor according to claim 6, further comprising:
    an edge sensor provided on a downstream side of the first opening in the insertion direction and on an upstream side of the first concave portion or near the first concave portion, and configured to detect that an edge of the object has passed while the object is moving in the insertion direction.

8. A paper-type discrimination device comprising:
    the optical sensor according to claim 1; and
    a controller configured to discriminate a paper type of the object using reflection light from the object measured by the optical sensor.

9. The paper-type discrimination device according to claim 8, wherein
    the optical sensor includes a pressurizer configured to press the object against the wall, the paper-type discrimination device includes a paper-thickness sensor configured to measure a thickness of the object based on a displacement caused to the pressurizer when the pressurizer presses the object against the wall, and the paper-type discrimination device discriminates a type of the object using the reflection light and the thickness measured by the paper-thickness sensor.

10. The paper-type discrimination device according to claim 9, wherein the pressurizer has a second opening, and the paper-thickness sensor includes a measuring part that abuts a portion of the object exposed at the second opening.

11. An image forming apparatus comprising: the paper-type discrimination device according to claim 8.

12. The image forming apparatus according to claim 11, further comprising: an adjuster configured to adjust an image-forming condition of the image forming apparatus according to the paper type of the object specified by the paper-type discrimination device.

13. An image forming apparatus comprising: the optical sensor according to claim 1.

14. The optical sensor according to claim 1, wherein the first concave portion is positioned on a wall side with respect to a position of the object to be measured, and wherein the first concave portion is a recess formed within a plane of the wall.

* * * * *